United States Patent [19]

Schulman

[11] 4,345,603

[45] Aug. 24, 1982

[54] IMPLANTABLE BATTERY MONITORING MEANS AND METHOD

[75] Inventor: Joseph H. Schulman, Los Angeles, Calif.

[73] Assignee: Pacesetter Systems, Inc., Sylmar, Calif.

[21] Appl. No.: 122,352

[22] Filed: Feb. 19, 1980

[51] Int. Cl.³ ............................................. A61N 1/36
[52] U.S. Cl. ............................................. 128/419 PT
[58] Field of Search ................. 128/419 PG, 419 PS, 128/419 PT, 419 R, 213, 260, 1 R

[56] References Cited

U.S. PATENT DOCUMENTS

| | | | |
|---|---|---|---|
| 3,738,371 | 6/1973 | Raddi et al. | 128/419 PS |
| 3,783,877 | 1/1974 | Bowers | 128/419 PS |
| 4,055,189 | 10/1977 | Auerbach et al. | 128/419 PT |
| 4,082,097 | 4/1978 | Mann et al. | 128/419 PS |
| 4,102,346 | 7/1978 | Fulker | 128/419 PS |
| 4,120,307 | 10/1978 | Jirak et al. | 128/419 PT |
| 4,142,533 | 3/1979 | Brownlee et al. | 128/419 PT |
| 4,231,027 | 10/1980 | Mann et al. | 128/419 PT |

Primary Examiner—William E. Kamm
Attorney, Agent, or Firm—John F. Buskirk

[57] ABSTRACT

A method and apparatus for monitoring the status of a battery in an implantable device for a human, the device being a tissue stimulator, drug dispensing apparatus, or the like. More specifically, a battery monitoring apparatus is disclosed whereby a user is sensually stimulated whenever an implanted battery exhibits predetermined characteristics. In one embodiment, the internal resistance of a battery is periodically monitored by loading the battery at predetermined intervals. When the internal resistance exhibits a predetermined characteristic, a battery alarm circuit is activated which causes a small voltage differential to be applied under and across the skin of the user, thereby creating a mildly tingling sensation in his skin. This tingling sensation alerts the user that the battery needs to be replaced or recharged. A magnet is provided for externally disabling the monitoring apparatus after the user has been alerted that the battery needs replacement. In a further embodiment, the alarm circuitry activates an audio signal generator which provides an audibly detectable beep when the battery needs to be replaced or recharged. In a still further embodiment, the battery output voltage is compared to a predetermined reference voltage source within the implantable device. The user is sensually stimulated whenever the battery output voltage, or a voltage related to the battery output voltage, drops below the predetermined reference voltage.

29 Claims, 7 Drawing Figures

IMPLANTABLE BATTERY MONITORING MEANS AND METHOD

BACKGROUND OF THE INVENTION

The invention relates to a monitoring means and method for batteries contained within implantable devices for a human.

Implantable devices, such as heart pacemakers, drug dispensing apparatus, and the like, are utilized to provide life-sustaining functions at appropriate locations within a user. These devices typically utilize an implantable battery as a power means. Although these batteries have long life, they do periodically need replacing or recharging. Since the life of a user frequently depends upon the battery providing adequate power to his implanted device, it is essential that the battery does not fail during use. For example, in conventional pacemakers, periodic battery replacements or recharges are conducted. These replacements sometimes require surgical operations to remove the pacemaker, and are sometimes more frequent than necessary in order to insure a replacement prior to battery failure. In some conventional pacemakers, a slowing down of the heartbeat is relied on as a warning to a user that battery failure is eminent. However, such a slowing is not sensually perceptible at any one time, but rather results in a general tiredness or the like. There has long been a need for a battery monitor which will immediately alert a user that this battery needs replacing or recharging without his having to go to a doctor's office for a test. The invention solves the above problem by providing the user with a positive, easily identifiable alarm signal whenever his battery needs replacement or recharging.

SUMMARY OF THE INVENTION

The invention provides a battery status indicator having a means for monitoring a characteristic of the battery, and a means responsive to the monitoring means for alerting a user when the battery voltage exhibits a predetermined characteristic which indicates that the battery should be replaced. The means responsive to the monitoring means includes a means for sensually stimulating the user whenever the battery voltage exhibits the predetermined characteristic. The invention also provides a method for monitoring an implantable battery.

In an exemplary embodiment of the invention, the internal impedance of the battery is periodically monitored. When this internal impedance exhibits a predetermined characteristic, an alarm circuit is activated which provides stimulating pulses near the skin of the user, the stimulating pulses providing a mildly tingling sensation. The tingling sensation alerts the user that the battery needs to be recharged or replaced. In another embodiment of the invention, an audio signal generator implanted in conjunction with the implantable device is activated, the generator providing periodic, audibly detectable beeps. The audio beeps also vibrate the skin lightly, thereby providing a further sensual stimulation to the user. The invention also provides a means for deactivating the alarm circuit once the user has been alerted that the battery needs replacing or recharging. In a still further embodiment of the invention, a voltage related to the battery output voltage is periodically compared to a reference voltage. An alarm means is activated when the reference voltage exceeds the voltage related to the battery output voltage.

DETAILED DESCRIPTION

Detailed illustrative embodiments of the invention disclosed herein exemplify the invention and are currently considered to be the best embodiments for such purposes. However, it is to be recognized that other means for sensually stimulating a user when an implanted battery is going to fail, and other means for determining the charge status of the battery could be utilized. Accordingly, the specific embodiments disclosed are only representative in providing a basis for the claims which define the scope of the present invention.

As previously explained, the invention provides a means for sensually stimulating a user of an implantable device having a self-contained battery however the battery is exhibiting characteristics indicative of an impending battery failure. In one embodiment of the invention, a means is provided whereby when the internal impedance of the battery reaches a predetermined level, the device user will feel a mild, tingling sensation in the skin adjacent to the implanted device. In another embodiment of the invention, a periodically repeating audio signal is provided. In this embodiment, the user is audibly alerted to impending battery failure as well as feeling a slight vibration in the skin adjacent to the implanted device whenever an audio signal is generated. A means is also provided whereby the user can inhibit the warning features of the invention once having been initially alerted that the implanted battery needs replacing or recharging. In a still further embodiment the user is alerted whenever the battery output voltage drops below a predetermined level related to a reference voltage.

Figure 1:
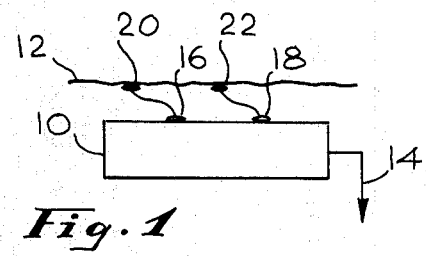
FIG. 1 is a side elevational view of an implanted tissue stimulator incorporating a battery status indicator provided by the invention.

Referring now to FIG. 1, an implantable tissue stimulator 10 is shown located beneath the skin 12 of a user. A stimulating electrode 14 is provided, the electrode 14 being used, for example, for stimulation of the user's heart. A first warning electrode 16 and a second warning electrode 18 are provided for applying a voltage potential across the flesh of the user. Extending electrodes 20 and 22 are connected to the first and second warning electrodes 16 and 18, respectively. Although separate warning electrodes are shown, for certain configurations of the tissue stimulator 10, the case itself can be formed of a conducting material and comprises one of the warning electrodes. Thus, only one separate warning electrode would have to be provided on the surface of the tissue stimulator 10. In addition, it is not necessary that there be extending electrodes 20 and 22, and just the warning electrodes 16 and 18 could be utilized.

Figure 2:
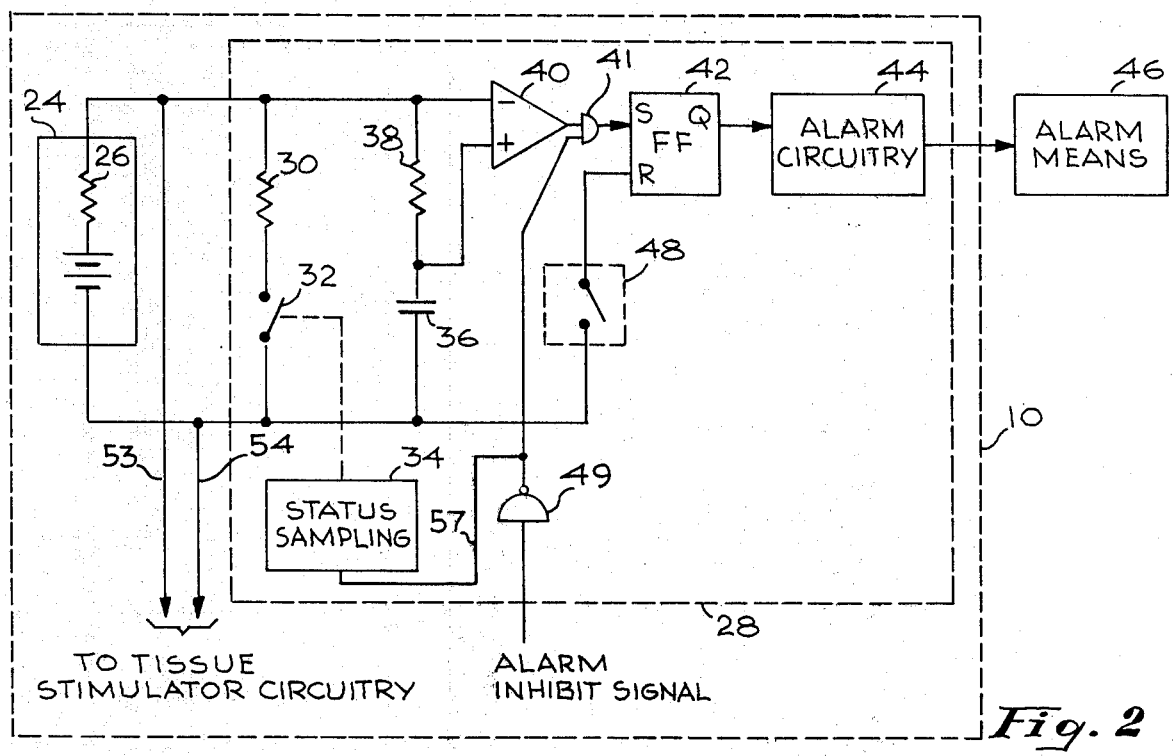
FIG. 2 is a circuit and block diagram of the battery status indicator.

Referring to FIG. 2, the implantable tissue stimulator 10 includes a battery 24 which has an equivalent internal impedance 26. The output terminals of the battery 24 are provided to a battery monitoring and alarm circuit 28. The circuit 28 includes a loading resistor 30 which can be connected across the output terminals of the battery 24 by a loading switch 32 which is closed at periodic intervals by a status sampling circuit 34. A biasing capacitor 36 and discharge resistor 38 provide inputs to a voltage comparator 40, which could be an operational amplifier. The voltage comparator is connected through an inhibiting AND gate 41 to a one-shot activating flip-flop 42. Alarm circuitry 44 and an alarm means 46 are also provided. A magnetically activated deactivating switch 48 provides a means for resetting the activating flip-flop 42. An inverter 49 is connected to one input of the inverting AND gate 41.

In operation, the voltage output from the battery 24 provides a charge build-up on the biasing capacitor 36 that is related to the output voltage of the battery 24 when powering the tissue stimulator circuitry (not shown). The voltage across the biasing capacitor 36 is provided as the plus input to the voltage comparator 40. The status sampling circuit 34 is chosen to close the loading switch 32 at predetermined periodic time intervals. Although the loading switch 32 is shown functionally as a switch, transistor switches or the like could be utilized. Whenever the loading switch 32 is in a closed condition, the loading resistor 30 is placed across the battery 24 output terminals, thereby resulting in an additional current through the battery 24 and its equivalent internal impedance 26. As the battery 24 ages, its equivalent internal impedance 26 increases. Thus, when the loading resistor 30 causes an additional current to flow through the battery, an additional voltage drop occurs across the equivalent interval impedance 26. This causes the voltage output of the battery as experienced by the negative input of the voltage comparator 40 to drop. The positive input however, which is represented by the voltage across the capacitor 36, does not exhibit this rapid drop because of the time constant provided by the discharge resistor 38. Thus, the voltage differential experienced by the voltage comparator 40 is related to the value of the equivalent internal impedance 26. The voltage comparator 40 is chosen so that whenever the voltage differential between that across the biasing capacitor 36 and the output by the battery 24 exceeds a predetermined amount, a set signal from the voltage comparator 40 is provided as one input to the inhibit AND gate 41. An alarm inhibit signal, which could be substantially in time-coincidence with a tissue stimulation pulse, is connected through the inverter 49 to the other input of the inhibit AND gate 41, thereby preventing the alarm means from being activated by a current surge through the battery caused by generation of a tissue stimulation pulse. The output of the inhibit AND gate sets the activating flip-flop 42. Once set, the activating flip-flop 42 remains set until reset by an external resetting means to be explained below. The output of the activating flip-flop 42 turns on alarm circuitry 44 which in turn activates an alarm means 46 which in this embodiment is the current producing warning electrodes described in conjunction with FIG. 1.

Additionally, the output of the inverter 49 is provided to the status sampling circuit 34 via an interconnection line 57. This signal is used to correlate operation of the status sampling circuit 34 so that the loading switch 32 will not be closed during tissue sampling intervals. Of course, if the sampling time interval is long with respect to the time of a tissue stimulation pulse, then the interconnection shown at 57 would not be required.

The inhibit AND gate 41 and the inverter 49 could be eliminated if the implanted device were of the type that did not draw current pulses from the battery 24. Or, it could be configured so that large current pulses are not drawn. For example, an RC circuit could be provided across two leads 53 and 54 leading to the stimulator circuitry. The resistor could be in series with line 53 and the capacitor in parallel across lines 53 and 54, the capacitor being connected to line 53 at the resistor terminal not directly connected to the battery.

As previously explained, the one-shot activating flip-flop 42, once set, can only be reset by an external resetting means. The deactivating switch 48 is a magnetic switch, which, when magnetically coupled to an external magnet means, closes, thus resetting the activating flip-flop 42. A user of the tissue stimulator, once having been warned that its battery needs replacing or recharging, may wish to deactivate the alarm means 46 until the battery is either recharged or replaced. Although the battery monitoring means described above is of the type wherein the equivalent internal impedance of the battery is monitored, it will be readily apparent that other types of monitoring means could be utilized to set the activating flip-flop 42. For example, an output voltage monitor of which there are many types could be provided to monitor other characteristics of an implantable tissue stimulator such as stimulating pulse height, width, or the like, the monitor setting the flip-flop 42 whenever the output voltage drops below a predetermined level.

Although the deactivating switch 48 has been chosen in this embodiment to be a magnetic switch, other types of switches for resetting the activating flip-flop 42 could be utilized. Examples of other switch types include a pressure sensitive switch responsive to the user pressing against skin adjacent to the implanted tissue stimulator, a switch responsive to mechanical vibrations, a switch responsive to a transmitted audio signal, a switch responsive to a light beam irradiating the skin adjacent to the implanted tissue stimulator, a switch responsive to an alternating magnetic field, or a switch responsive to an rf signal having a predetermined frequency. These types of switches could be utilized in conjunction with a threshold detector, the output of which could be utilized to reset the activating flip-flop 42.

Figure 3:
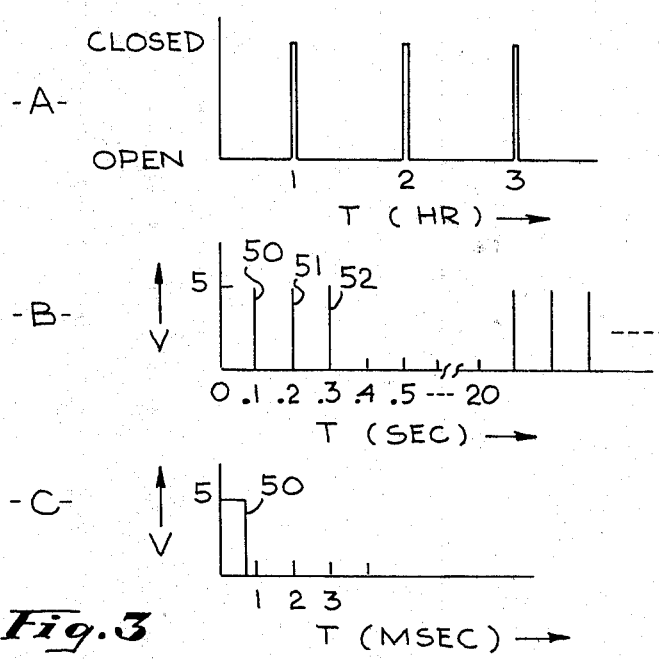
FIGS. 3A, 3B, and 3C are waveform diagrams of pulses chosen to provide a tingling sensation in the skin of a user.

For the embodiment shown in FIG. 1 in which the alarm means 46 comprises two extending electrodes 20 and 22, the alarm circuitry 44 provides signals in accordance with the waveforms shown in FIGS. 3A, 3B and 3C. Referring to FIG. 3A, the status sampling circuit 34 is chosen so that the loading switch 32 is closed every hour for a quarter of a second as shown in FIG. 3A. Although hourly intervals have been chosen for this illustrative embodiment, any other appropriate interval could also be chosen such as once a day, once a week or once a month. The loading switch 32 remains closed for approximately one-quarter of a second in order to minimize current drain from the battery and also to insure that the voltage differential across the biasing capacitor 36 will remain substantially constant during the sampling interval. Accordingly, the discharge resistor 38 is chosen to provide a time constant consistent with maintaining a substantially constant charge on the biasing capacitor 36 during the one-quarter second sampling interval. As previously explained, when the voltage differential exceeds a predetermined amount, the activating flip-flop 42 is set by an output voltage from the voltage comparator 40. The alarm circuitry 44 is chosen to provide three five-volt output pulses 50, 51 and 52 every 20 seconds, the three pulses 50, 51 and 52 being spaced apart by 100 milliseconds as shown in FIG. 3B, each pulse being three-quarters of a millisecond wide as shown in FIG. 3C. The five-volt pulses above-described will provide a tingling sensation to a user when the extending electrodes 20 and 22 are spaced apart enough to provide approximately 500 ohms resistance therebetween.

Figure 5:
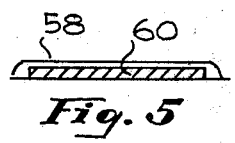
FIG. 5 is a cross-sectional view taken along lines 5—5 of FIG. 4.
Figure 4:
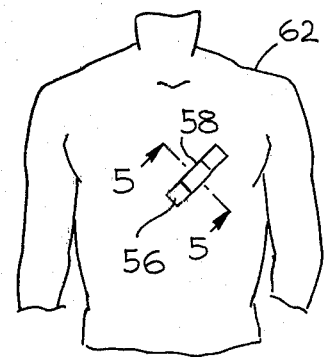
FIG. 4 is an elevational view showing a magnet fixed against the skin of a user for inhibiting the battery status indicator.

As previously explained, the deactivating switch 48 can be closed by an externally located magnet placed in magnetically-coupled relationship therewith. When momentarily closed, the magnetically activated switch 48 will reset the activating flip-flop 42, which in turn will remain reset until the next time a status sampling pulse is generated. If the status sampling interval is chosen to be a week or a month, the tingling sensation will be a regular reminder to a user. If the status sampling interval is short, such as one hour, the user can tape a magnet over the implanted tissue stimulator until the battery is replaced. Referring to FIG. 4, a user 54 is shown having a strip of adhesive 56 located on a body portion adjacent to the implantable tissue stimulator 10. A central portion 58 of the adhesive strip 56 contains a small flat magnet 60. Referring to FIG. 5, the magnet 60 is shown contained within the adhesive strip central portion 58. In operation, the user, once feeling the tingling sensation, can attach the adhesive strip 56 to his body, thereby preventing him from feeling the sensual effects of the alarm means 46 while he is proceeding to a location at which the battery can either be replaced or recharged.

Figure 6:
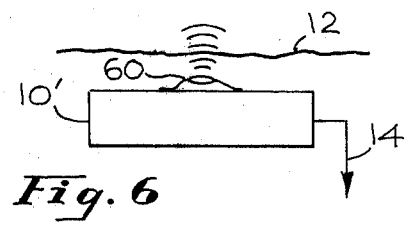
FIG. 6 is a diagrammatic representation of a further embodiment of the invention in which an audio signal is utilized to alert the user of a failing battery.

In a further embodiment of the invention shown in FIG. 6, an implantable tissue stimulator 10' is shown in which the alarm means includes an audio signal generator 60. In this embodiment, the alarm circuitry provides an audio signal beep every five seconds for one-half second. The beep is heard by the user, and also the vibration of the audio signal propagating to the surface of the user's skin 12 is felt by the user. It is obvious that the beeper could also be chosen to produce only a vibrational signal or only an audio signal.

Figure 7:
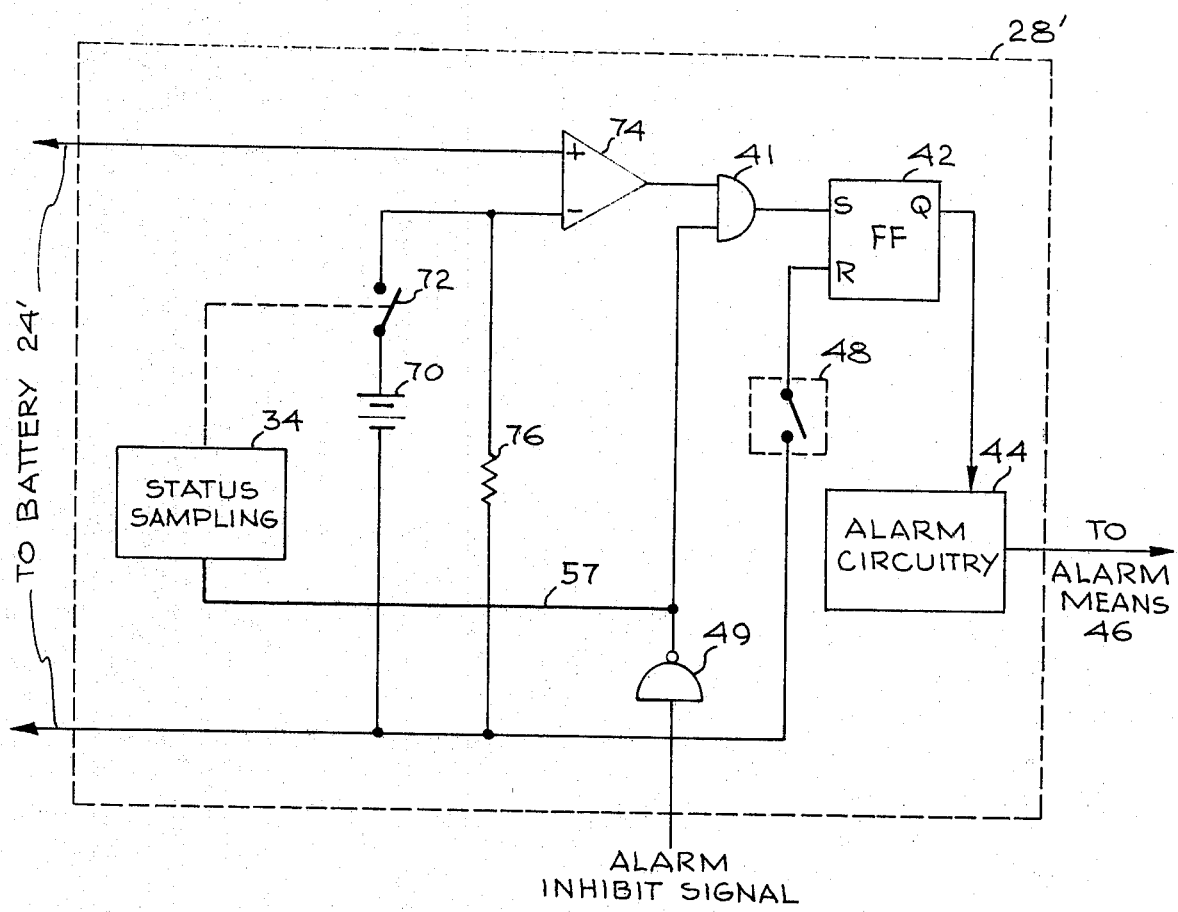
FIG. 7 is a circuit and block diagram of a further embodiment of the battery status indicator.

A further embodiment of the battery monitoring and alarm circuit 28' is shown in FIG. 7. For ease of description, circuit elements identical to those in the FIG. 2 embodiment have the same numerical identifiers. Certain types of lithium and nickle cadmium batteries have characteristics wherein the internal resistance remains substantially constant throughout the life of the battery, and the output voltage drops as battery life remaining decreases. The battery monitoring means shown in FIG. 2 would be unsuitable for this type of battery because its output voltage would remain relatively constant during each sampling interval. The battery monitoring and alarm circuit 28' shown in FIG. 7 causes the alarm means 46 to be activated even though the battery 24' maintains a substantially constant internal resistance. The circuit 28' utilizes the same status sampling circuit 34, inhibiting AND gate 41, activating flip-flop 42, alarm circuitry 44, deactivating switch 48 and inverter 49 as in the FIG. 2 embodiment. A reference voltage source 70 is connected through a status sampling switch 72 to a minus input of a voltage comparator 74. A loading resistor 76 is also connected across the minus input of the voltage comparator 74 and the battery 24' return line. The plus input to the voltage comparator 74 is connected to the positive terminal of the battery 24'. In operation, the status sampling circuit 34 periodically closes the status sampling switch 72, thereby causing the reference voltage source 70 output voltage to be applied to the minus input of the voltage comparator 74. If the reference voltage exceeds the battery 24' output voltage, the output of the voltage comparator 74 becomes high and will set the activating flip-flop 42 so long as the output of the inverter 49 is high as explained in the FIG. 2 embodiment. Operation of all the other circuit elements is as previously explained. If a voltage reference source 70 having a higher output voltage than desired is utilized, a dropping resistor can be added in series with the status sampling switch 72. Alternatively, a resistor could be placed in series with the plus input of the voltage comparator 74 in order to lower the battery input voltage to the voltage comparator 74, thereby allowing a lower reference voltage source 70 to be utilized. A zener diode in lieu of the reference voltage source 70 could be connected across the battery 24' output terminals, the voltage drop across the zener being the reference voltage provided to the minus input of the voltage comparator 74. The battery output voltage, appropriately scaled, would be provided to the plus input of the voltage comparator 74.

It should now be apparent that an implanted battery monitoring means has been described wherein the user is alerted when the battery output voltage exhibits a predetermined characteristic. A means has also been described whereby the user can deactivate the alarm means after he has been alerted that the battery needs replacing or recharging.

What is claimed is:
1. In combination:
an implantable device having a battery contained therein;
a load means for drawing current from said battery;
first means for providing a first voltage related to the output voltage of said battery;
second means for periodically applying said load means to said battery, thereby generating a second voltage related to said loaded battery output voltage;
comparison means responsive to said first and second voltages for generating an output signal having a predetermined characteristic when said first and second voltages have a predetermined relationship with respect to each other, said output signal being related to the internal impedance of said battery; and
third means responsive to said output signal for indicating that said predetermined characteristic is present.
2. The combination of claim 1 wherein said third means comprises means for alerting the device user when said output signal has said predetermined characteristic.
3. The combination of claim 2 wherein said implantable device is of the type having an alarm inhibit signal at appropriate time increments, said combination further comprising means responsive to said alarm inhibit signal for preventing said third means from being responsive to said output signal.

4. The combination of claim 2 wherein said third means comprises alarm means to sensually stimulate said user when said output signal exhibits said predetermined characteristic.

5. The combination of claim 4 wherein said alarm means comprises an audio signal generator.

6. The combination of claim 4 wherein said alarm means comprises electrode means for producing an electric current through the tissue of said user thereby producing a mild tingling sensation.

7. The combination of claim 2 wherein said comparison means comprises:
a voltage comparator having first and second voltage signal inputs, and a predetermined output voltage when said first signal is lower than said second signal by a predetermined amount, said predetermined output voltage being said output signal;
means for providing said first voltage to said voltage comparator first signal input; and
means for providing said second voltage to said voltage comparator second signal input.

8. The combination of claim 7 wherein said means for providing said second voltage comprises:
a resistor;
a capacitor connected to said resistor, said resistor-capacitor combination being connected across said battery; and
means for connecting said capacitor/resistor interconnection point to said voltage comparator second signal input.

9. The combination of claim 8 wherein said third means responsive to said output signal comprises:
a one-shot flip-flop;
means for setting said flip-flop when said voltage comparator provides said output signal; and
means responsive to said flip-flop being in a set condition for sensually stimulating said user.

10. The combination of claim 9 wherein said third means further comprises means for resetting said flip-flop.

11. The combination of claim 10 wherein said means for resetting comprises;
a magnetically activated switch; and
a magnet for activating said switch.

12. In combination:
an implantable device having a battery contained therein;
a voltage comparator having first and second voltage signal inputs and a predetermined output voltage when said second signal is greater than said first signal;
means for providing a voltage related to the output voltage of said battery to said voltage comparator first signal input;
a reference voltage source;
means for periodically applying said reference voltage to said voltage comparator second signal input, thereby resulting in said voltage comparator providing said predetermined output voltage when said reference voltage is greater than said first voltage signal input; and
means responsive to said predetermined output voltage for indicating said reference voltage is greater than said first voltage signal input.

13. The combination of claim 12 wherein said means responsive to said predetermined output voltage comprises means for alerting the device user that said reference voltage is greater than said first signal input.

14. The combination of claim 13 wherein said reference voltage source comprises a battery.

15. The combination of claim 14 wherein said means responsive to said predetermined output voltage comprises;
a one-shot flip-flop;
means for setting said flip-flop when said voltage comparator provides said predetermined output voltage; and
means responsive to said flip-flop being in a set condition for sensually stimulating said user.

16. The combination of claim 15 wherein said means responsive to said predetermined output voltage further comprises means for resetting said flip-flop.

17. The combination of claim 16 wherein said means for resetting comprises:
a magnetically activated switch; and
a magnet for activating said switch.

18. In combination:
an implantable device having a self-contained battery;
a load means for drawing current from said battery;
means for connecting said load means across said battery at predetermined time intervals;
means for generating an output signal related to a decrease in battery output voltage when said load means is connected across said battery; and
means responsive to said output signal for indicating when said battery output voltage is at a predetermined level that is lower than said battery unloaded output voltage.

19. The combination of claim 18 further comprising alarm means responsive to said output signal for sensually stimulating a user of said implantable device.

20. The combination of claim 19 wherein said implantable device is of the type having an alarm inhibit signal at appropriate time increments, said combination further comprising means responsive to said alarm inhibit signal for inhibiting said alarm means.

21. The combination of claim 19 wherein said load comprises a resistor connected to one of said battery output terminals and said means for connecting comprises;
a switch means connected in series between said resistor and the other battery output terminal; and
a sampling circuit to close said switch means for a predetermined time increment at predetermined time intervals.

22. The combination of claim 19 wherein said means for generating comprises:
means for comparing the voltage of said battery when said load is connected across said battery and when said load is not connected across said battery, said means for comparing providing said output signal having said predetermined characteristics when the ratio of said battery voltage when said load is connected across said battery to said battery voltage when said load is not connected across said battery is below a predetermined value; and
means for providing an alarm signal to said alarm means when said means for comparing provides said output signal having said predetermined characteristics.

23. The combination of claim 22 wherein said means for comparing comprises;
a voltage comparison means for providing said output signal;

a serially connected capacitor/resistor combination connected across said battery output terminals;

means for connecting the interconnection point of said capacitor and resistor to one input of said voltage comparison means; and means for connecting the output voltage of said battery to the other input of said voltage comparison means whereby said voltage comparison means will provide said output signal having said predetermined characteristics when the voltage at said one input with respect to the voltage at said other input drops below a predetermined ratio.

24. The combination of claim 23 wherein said means for providing an alarm signal comprises a one-shot flip-flop which is set by said output signal.

25. The combination of claim 19 wherein said alarm means comprises electrode means for passing an electrical current through the tissue of said user, thereby causing a tingling sensation.

26. The combination of claim 19 wherein said alarm means comprises an audio signal generator for providing an audio signal perceptible to said user.

27. In combination:

an implantable device having a self-contained battery;

a reference voltage source;

means for providing a first voltage related to said battery output voltage;

comparison means for comparing said first voltage to said reference voltage; and alarm means responsive to said comparison means for sensually stimulating a user of said implantable device.

28. The combination of claim 27 wherein said comparison means comprises a voltage comparator having said related first voltage and said reference voltage as inputs, said comparator providing a predetermined output voltage when said reference voltage is greater than said first voltage, and said alarm means is responsive to said predetermined output voltage.

29. A method for monitoring the status of a battery in an implantable device comprising the steps of:

providing a first voltage related to the output voltage of said battery;

periodically applying a load to said battery, thereby generating a second voltage related to said loaded battery output voltage;

generating in response to said accessing and periodically applying steps an output signal having a predetermined characteristic when said first and second voltages have a predetermined relationship with respect to each other, said output signal being related to the internal impedance of said battery; and developing an alarm signal in response to said output signal for alerting a user that said first and second voltages have said predetermined relationship with respect to each other.

* * * * *